United States Patent [19]

Mezrich et al.

[11] 4,197,749
[45] Apr. 15, 1980

[54] ULTRASONIC WAVE ENERGY ELECTRONIC B-SCAN IMAGING APPARATUS

[75] Inventors: Reuben S. Mezrich, Rocky Hill; David H. R. Vilkomerson, Princeton, both of N.J.

[73] Assignee: RCA Corporation, New York, N.Y.

[21] Appl. No.: 964,899

[22] Filed: Dec. 5, 1978

[30] Foreign Application Priority Data

Dec. 12, 1977 [GB] United Kingdom ............... 51685
Dec. 12, 1977 [GB] United Kingdom ............... 51686

[51] Int. Cl.² .......................................... G01N 29/00
[52] U.S. Cl. ................................... 73/625; 367/7; 340/5 MP
[58] Field of Search ............... 73/625, 626, 628, 606, 73/607; 128/660; 340/1 R, 3 R, 5 MP, 9; 310/336

[56] References Cited

U.S. PATENT DOCUMENTS

| | | | |
|---|---|---|---|
| 2,700,895 | 2/1955 | Carson | 73/626 |
| 3,979,711 | 9/1976 | Maginness et al. | 73/579 |
| 4,012,952 | 3/1977 | Dory | 73/612 |
| 4,131,024 | 12/1978 | Mezrich | 73/626 |

Primary Examiner—Stephen A. Kreitman
Attorney, Agent, or Firm—George J. Seligsohn; Samuel Cohen

[57] ABSTRACT

A transducer comprising a longitudinal bar of piezoelectric material having one longitudinal face substantially covered with a first electrode and the opposite longitudinal face in contact with a predetermined plural number of separate electrodes spaced along the length thereof, permits all detected echoes to be processed by a single low input impedance amplifier permanently coupled to the first electrode.

5 Claims, 5 Drawing Figures

ULTRASONIC WAVE ENERGY ELECTRONIC B-SCAN IMAGING APPARATUS

This invention relates to a high resolution pulse-echo ultrasonic imaging display system and, more particularly, to such a system employing electronic B-scan imaging apparatus.

Reference is made to currently allowed U.S. patent application Ser. No. 766,564, filed Feb. 7, 1977, now U.S. Pat. No. 4,131,021, by Mezrich et al. and assigned to the same assignee as the present application. Application Ser. No. 766,564 discloses many embodiments of a high resolution pulse-echo ultrasonic imaging display system, including some which employ electronic C-scan imaging apparatus. The B-scan imaging apparatus of the present application makes use of certain features of the electronic C-scan imaging apparatus embodiment shown in FIG. 6 of the aforesaid patent application Ser. No. 766,564. However, the B-scan imaging apparatus of the present invention also incorporates certain novel features, which make for a simpler, less expensive, but more reliable high resolution pulse-echo ultrasonic imaging B-scan display system than was heretofore available.

In accordance with the principles of the present invention, a novel fixed transducer generates a scanning beam of pulsed ultrasonic wave energy, which insonifies a structure to be imaged. A single amplifier, having a low-impedance input, is permanently connected to a given electrode of the transducer. This single amplifier processes all detected echoes returned to the fixed transducer from the insonified structure. The novel transducer comprises a longitudinal bar of piezoelectric material having one of two opposite longitudinal faces thereof substantially covered by the aforesaid given electrode. Substantially equally spaced along the length of the other of the two longitudinal faces of the bar is each of a set of a predetermined plural number of separate electrodes. Successive ones of a series of ultrasonic frequency pulses are applied, in turn, to each individual one of the set of separate electrodes.

Figure 1:
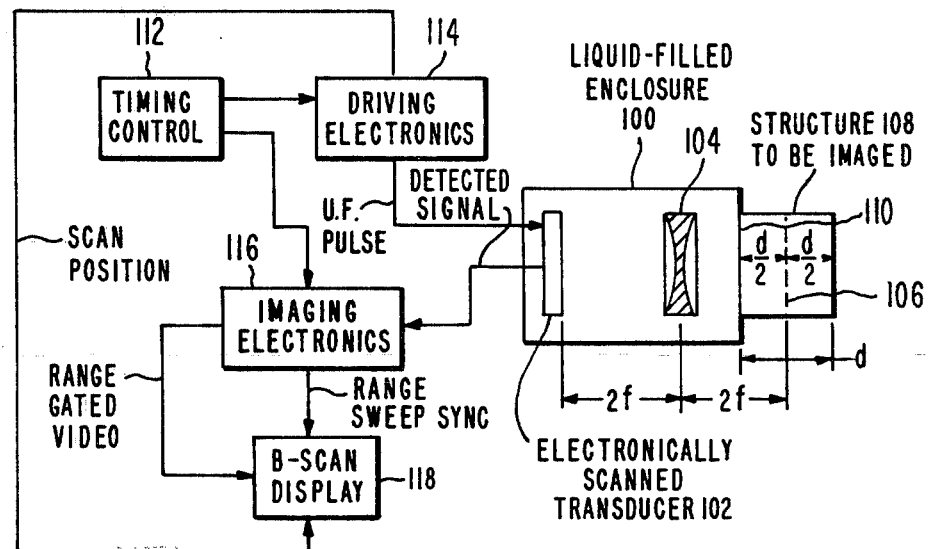
FIG. 1 is a block diagram of a B-scan pulse-echo ultrasonic wave energy imaging system incorporating the present invention.

Referring to FIG. 1, situated within liquid-filled enclosure 100 is electronically-scanned electro-acoustic transducer 102 and acoustic lens 104 having a focal length f. The physical aperture of lens 104, or the aperture of an irismear lens 104, whichever is smaller, determines the effective imaging aperture of the transducer-lens combination. As indicated, lens 104 is situated at a distance of 2f from transducer 102. Therefore, in accordance with the principles of geometric optics, transducer 102 is imaged in image plane 106 located at the same distance 2f on the other side of lens 104. Conversely, any structure situated in image plane 106 is imaged at transducer 102.

As taught in the aforesaid patent application Ser. No. 766,564, an acoustic lens exhibits a depth of field proportional to the wavelength of the incident acoustic (ultrasonic) wave energy and inversely proportional to the square of the ratio of the effective aperture to the focal length of the acoustic lens. For purposes of describing the present invention, it is assumed that the depth of field exhibited by lens 104 is at least one-half the depth d of structure 108 to be imaged.

The front wall 110 of enclosure 100 is composed of a material, such as rubber, which propagates therethrough ultrasonic wave energy incident thereon from the propagating liquid filling enclosure 100. Structure 108, which may be living tissue of a human being, is non-homogeneous and, therefore, has ultrasonic propagating characteristics at different spatial locations thereof which vary in a complex manner in accordance with the detailed make-up of structure 108. Structure 108 is situated with one surface thereof in contact with front wall 110 of enclosure 100.

Transducer 102 (shown in detail in FIG. 2) is intermittently energized, under the control of timing control 112, by an ultrasonic frequency (UF) pulse from driving electronics 114. In response thereto electronically scanned transducer 102 launches a beam of pulsed ultrasonic wave energy, which is propagated through the liquid filling enclosure 100 and through structure 108. This ultrasonic beam is focused by lens 104 to a point in image plane 106 corresponding to the then-existing scan position of electronically scanned transducer 102. However, due to the fact that the depth of field of structure 108 includes the entire depth d thereof, the entire depth of the region of structure 108 then being insonified by the scanned beam of ultrasonic wave energy gives rise to reflected echoes, which are returned through lens 104 and imaged on electronically scanned transducer 102 after a time delay which is proportional to the range (distance) of the reflecting point within the structure 108 from transducer 102.

Transducer 102 in response to receiving an ultrasonic echo, derives a detected electrical signal, which is applied as an input to imaging electronics 116. Imaging electronics 116, under the control of a signal from timing control 112, applies a range-gated video signal to the intensity-control electrode of the cathode-ray-tube (CRT) of B-scan display 118. In addition, imaging electronics 116 derives a range sweep sync in time-synchronous relationship with the generation of each UF pulse for initiating a linear deflection of the electron beam of the CRT of B-scan display 118 in one of two orthogonal directions (e.g. horizontal). At the same time, the electron beam of the CRT of B-scan display 118 is deflected the other of the two orthogonal direction (e.g. vertical) in accordance with a scan-position signal from driving electronics 114. This results in an image of a certain scan position-depth plane of structure 108 being displayed on the face of the CRT of B-scan display 118.

Figure 2:
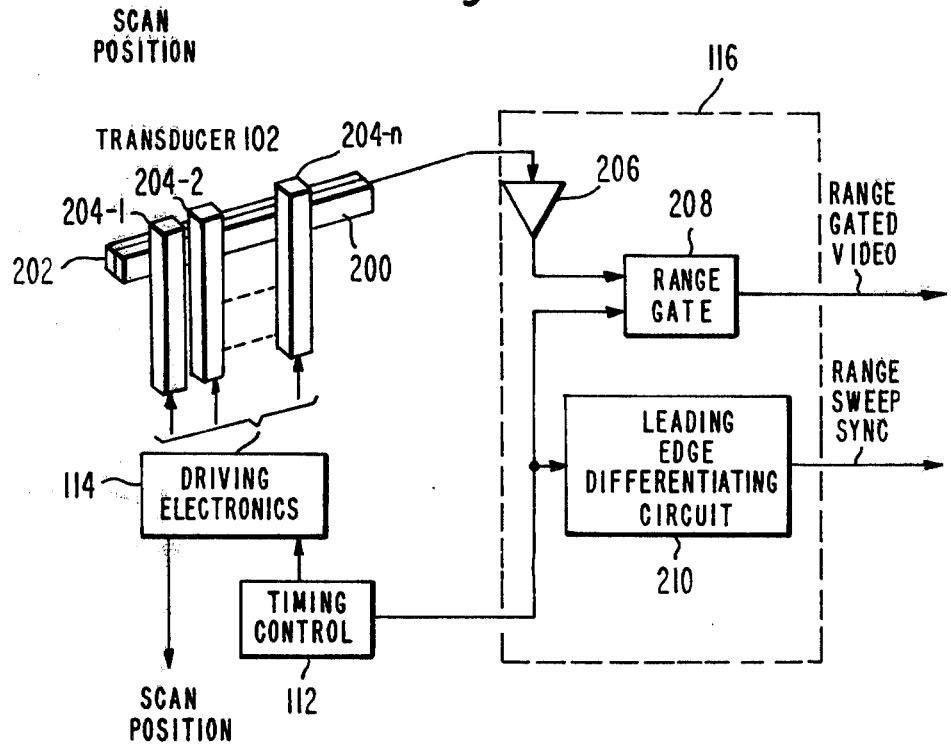
FIG. 2 shows in more detail the structure of the electronically scanned transducer and imaging electronics of FIG. 1.

As shown in FIG. 2, transducer 102 comprises longitudinal bar 200 of piezoelectric material. The back face of bar 200 is substantially covered by electrode 202. A set of n separate electrodes 204-1 . . . 204-n are in contact with the front face of piezoelectric bar 200. The predetermined number n is equal to the number of scans per frame (i.e. scan position resolution) required. The greater the value n, the greater the number of range sweeps in each displayed frame. In practice, the value of n is usually in the range of one-hundred to several hundred. Each electrode of the set of electrodes 204-1 ... 204-n ... is individually energized (in a manner described in detail below) by driving electronics 114.

Both applied UF pulses and detected echo signals are supplied by electrode 202 to the input of amplifier 206 of imaging electronics 116. Amplifier 206 should have a sufficiently low input impedance so that it provides a ground return for the driving pulse. Also such low input impedance insures that each relatively high amplitude applied UF pulse has substantially completely decayed before any echo from structure 108 is detected by transducer 102. This is necessary because detected echo signals have an amplitude vastly smaller than the amplitude of UF PULSE. The use of a low input impedance amplifier 206 eliminates the need for a conventional T-R switch to ensure that the UF pulses do not interfere with the detection the relatively extremely weak detected echoes.

In any event, the output of amplifier 206 is applied as an input to range gate 208 of imaging electronics 116. Range gate 208 is normally closed, but is maintained open during the occurrence of each range gate control pulse applied to range gate 208 from timing control 112. Each range gate control pulse, which occurs in time-synchronous relationship with the application of a UF pulse to transducer 102, maintains range gate 208 open during the entire time interval during which echoes within all of the structure 108 are being received by transducer 102. This results in range gate 208 forwarding all the detected signals from structure 108 as a range-gated video to B-scan display 118. The range sweep sync is derived by leading edge differentiating circuit 210 of imaging electronics 116 in time coincidence with the leading edge of each range gate control pulse from timing control 112.

Figure 3:
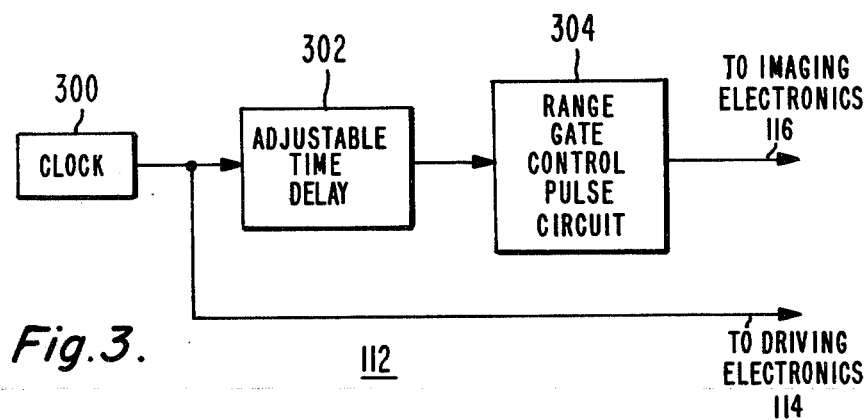
FIG. 3 is a block diagram showing in more detail the structural arrangement of the timing control of FIG. 1.

As shown in FIG. 3, timing control 112 includes clock 300 for periodically generating clocks at a repetition period at least slightly greater than the maximum round trip travel time of ultrasonic wave energy to any point within structure 108. Each clock is applied as a trigger to driving electronics 114. In addition, each clock is applied as a trigger input to adjustable time delay 302, which may comprise a monostable multivibrator. Adjustable time delay 302 is adjusted to provide a delay corresponding to the desired time of occurrence of the leading edge of a range gate control pulse. The output from adjustable time delay 302 is a delayed trigger which is applied as an input to range gate control pulse circuit 304. The range gate control pulse circuit 304 produces a pulse having a duration equal to the entire period during which it is desired that range gate 208 be open, so as to pass all detected signals from structure 108. The output from circuit 304 is applied as a control input to range gate 208 of imaging electronics 116, as described above.

Figure 4:
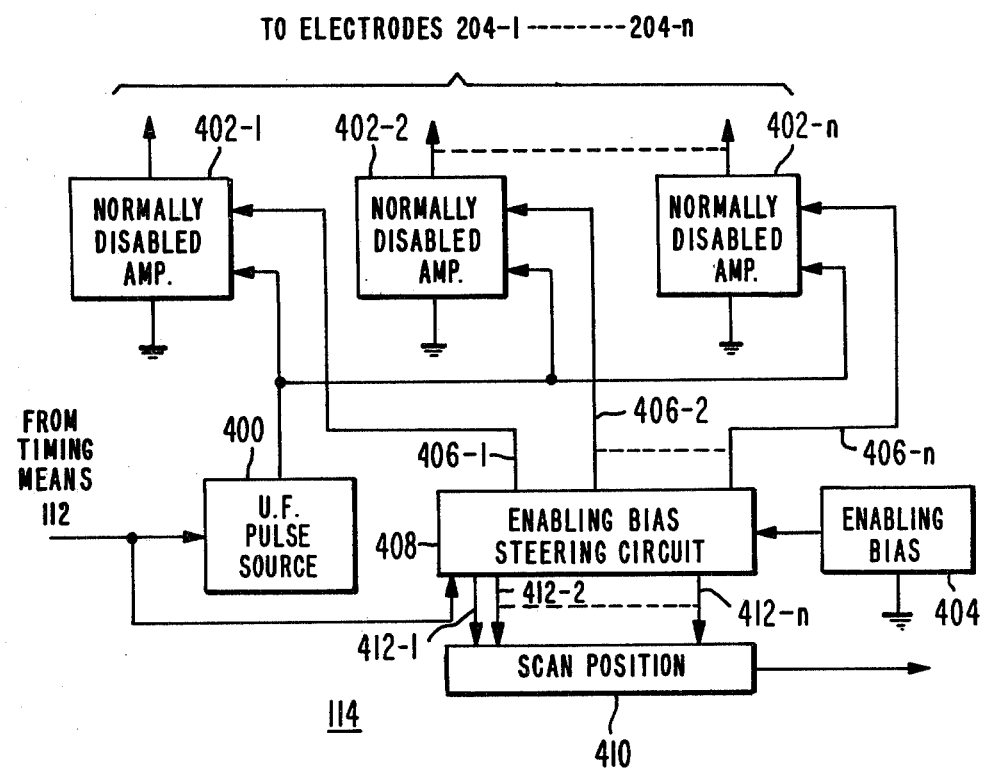
FIG. 4 is a block diagram showing in more detail the structural arrangement of the driving electronics of FIG. 1.

Driving electronics 114 may include UF pulse source 400 (FIG. 4), that produces a UF pulse in response to each clock from timing means 112 applied as a trigger thereto. Each UF pulse from source 400 is applied in parallel to every one of a set of n normally disabled amplifiers 402-1 ... 402-n. An enabling bias 404 for any one of amplifiers 402-1 ... 402-n is forwarded, in turn, through different selected ones of the first set of n outputs 406-1 ... 406-n of enabling bias steering circuit 408. More specifically, enabling bias steering circuit 408 may comprise a digital counter having a count capacity of n. The counter counts the clock triggers applied from timing means 112 to source 400. In addition, enabling bias steering circuit 408 may include a corresponding set of n normally opened electronic switches, each of which connects enabling bias 404 to a different one of outputs 406-1 ... 406-n. Each of these n switches is closed, one at a time, in accordance with the count then registered in the counter.

The order of closing these n switches of enabling bias steering circuit 408 may or may not, as desired, correspond with the order of the set of amplifiers 402-1 ... 402-n. In particular, if the order of closing of the set of n switches of enabling bias steering circuit 408 is such as to enable, in order, each of normally disabled amplifiers 402-1 ... 402-n, the range sweep raster of B-scan display 118 will be non-interlaced. However, if the order of enabling amplifiers 402-1 ... 402-n is to first enable, in turn, all the odd amplifiers and then, in turn, enable all the even amplifiers, the range sweep raster of B-scan display 118 is interlaced, in a manner similar that of a television raster. If the frame rate is very low, it may be desirable to provide interlacing with a higher degree than two (i.e. more than two fields per frame) to reduce flickering. In any case, each of the n switches of enabling bias steering circuit 408 can be associated individually in any selected order with outputs 406-1 ... 406-n to provide any type of interlacing desired. Alternatively, any type of interlacing may be selected in accordance with the manner of individual association of the outputs of amplifier 402-1 ... 402-n with the set of electrodes 204-1 ... 204-n.

Scan position circuit 410 may comprise a digital-to-analog converter, responsive to the count then registered in the counter of enabling biased steering circuit 408, which is applied thereto, through a second set of n outputs 412-1 ... 412-n from circuit 408. The arrangement is such that scan position circuit 410 derives a staircase-wave vertical deflection signal for B-scan display 118, which at any time exhibits a level that corresponds to the spatial position of the then-energized one of the set of electrodes 204-1 ... 204-n.

Figure 5:
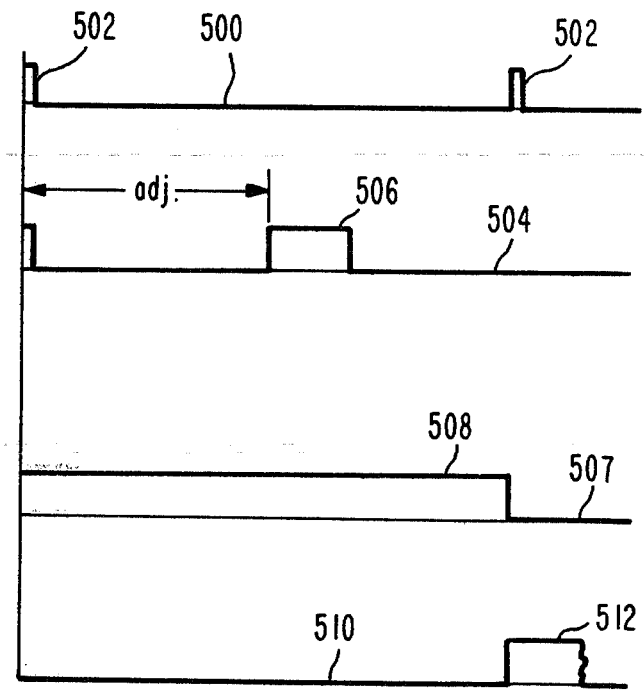
FIG. 5 is a timing diagram useful in explaining the operation of the present invention.

Graph 500 of FIG. 5 shows the relative time of occurrence of successive clocks generated by clock 300 of timing means 112. Graph 504 shows the relative time of occurrence of a range gate control pulse 506 derived by range gate control pulse circuit 304 of timing control 112. Graph 507 shows the time of enablement 508 of solely normally disabled amplifier 402-1. As indicated by graph 507 normally disabled amplifier 402-1 is enabled for substantially one entire clock period. However, if there are n amplifier, amplifier 402-1 amplifiers than remains disabled for the next (n−1) clock periods. Assuming non-interlaced operation, graph 510 shows the first portion of the time period of enablement 512 of normally disabled amplifier 402-2. Thus, each of the set of n normally disabled amplifiers 402-1 ... 402-n is enabled for a different single one of each set of n consecutive clock periods.

What is claimed is:

1. Ultrasonic wave energy electronic B-scan imaging apparatus comprising:
   an electro-acoustic transducer including a longitudinal bar of piezoelectric material, a given electrode substantially covering one of two opposite longitudinal faces of said bar, and a set of n separate electrodes disposed in spaced relationship along the length of the other of said two longitudinal faces, where n is a predetermined plural integer, driving electronics for applying a series of n ultrasonic frequency pulses to said transducer with each separate pulse in said series being applied to a different one of said set of n electrodes, and a single amplifier having its input coupled to said given-electrode for amplifying all detected echo signals received by said transducer from a structure to be imaged.

2. The apparatus defined in claim 1, wherein the input of said amplifier is permanently coupled to said first electrode, whereby all said ultrasonic frequency pulses are applied to the input of said amplifier, and wherein the input impedance of said amplifier is sufficiently low that it provides a ground return for every ultrasonic frequency pulse of said series and each ultrasonic frequency pulse substantially completely decays prior to the occurrence of detected echo signals from said structure to be imaged.

3. The apparatus defined in claim 1, wherein said n electrodes of said set are substantially equally spaced from each other.

4. The apparatus defined in claim 1, wherein said driving electronics includes means for deriving a B-scan position deflecting signal having a variable level which is an analog of the spatial position of that one of said set of n electrodes to which an ultrasonic frequency pulse has been then applied.

5. The apparatus defined in claim 4, wherein said n electrodes of said set are substantially equally spaced from each other.

* * * * *